US011709468B2

(12) United States Patent
Bollella

(10) Patent No.: US 11,709,468 B2
(45) Date of Patent: Jul. 25, 2023

(54) USER COMFORT CONTROL SYSTEM HAVING NON-INVASIVE BIO-PATCH

(71) Applicant: LIFE PATCH INTERNATIONAL, Irvine, CA (US)

(72) Inventor: Donald Bollella, Irvine, CA (US)

(73) Assignee: Life Patch International, Irvine, CA (US)

( * ) Notice: Subject to any disclaimer, the term of this patent is extended or adjusted under 35 U.S.C. 154(b) by 0 days.

(21) Appl. No.: 16/045,353

(22) Filed: Jul. 25, 2018

(65) Prior Publication Data

US 2019/0033806 A1 Jan. 31, 2019

Related U.S. Application Data

(60) Provisional application No. 62/536,938, filed on Jul. 25, 2017.

(51) Int. Cl.
*G05B 19/042* (2006.01)
*G06F 1/16* (2006.01)
(Continued)

(52) U.S. Cl.
CPC .......... *G05B 19/042* (2013.01); *A47C 21/042* (2013.01); *A47C 21/048* (2013.01);
(Continued)

(58) Field of Classification Search
CPC .......... G05B 2219/2614; G05B 19/042; A61B 5/6816; A61B 5/6824; A61B 5/01;
(Continued)

(56) References Cited

U.S. PATENT DOCUMENTS 4,329,999 A * 5/1982 Phillips .................. A61B 5/411
156/247
4,444,193 A * 4/1984 Fogt ..................... A61B 5/4266
422/424

(Continued)

FOREIGN PATENT DOCUMENTS

JP 2005-270401 A 10/2005
JP 3927495 B2 6/2007
(Continued)

OTHER PUBLICATIONS

VitalSense® Integrated Physiological Monitoring System, Instruction Manual, Mini Mitter Company, Inc. ,Bend, OR USA. 2003 (Year: 2003).*

(Continued)

*Primary Examiner* — Sunita Reddy
(74) *Attorney, Agent, or Firm* — Chang & Hale LLP

(57) ABSTRACT

User comfort control system having non-invasive bio-patch. In some embodiments, a system for providing comfort of a person can include a wearable patch configured to be attached to a skin of the person and sense a biological condition of the skin, and to transmit information representative of the sensed biological condition. The system can further include a controller configured to receive the information and generate a control signal. The system can further include an adjustment element associated with a furniture item implemented to support and provide comfort for the person. The adjustment element can be in communication with the controller and be configured to adjust a comfort level of the furniture item for the person in response to the control signal.

9 Claims, 14 Drawing Sheets

(51) Int. Cl.
   *A61B 5/00* (2006.01)
   *A47C 21/04* (2006.01)
   *A47C 31/12* (2006.01)
   *A61B 5/01* (2006.01)
   *A47C 31/00* (2006.01)

(52) U.S. Cl.
   CPC ............ *A47C 31/123* (2013.01); *A61B 5/443* (2013.01); *A61B 5/6824* (2013.01); *A61B 5/6833* (2013.01); *G06F 1/163* (2013.01); *A47C 21/04* (2013.01); *A47C 31/008* (2013.01); *A61B 5/01* (2013.01); *A61B 5/6816* (2013.01); *G05B 2219/2614* (2013.01)

(58) Field of Classification Search
   CPC ..... A61B 5/6833; A61B 5/443; A47C 31/123; A47C 21/042; A47C 31/008; A47C 21/04; A47C 21/048; G06F 1/163
   USPC ..................................................... 600/26–28
   See application file for complete search history.

(56) References Cited

U.S. PATENT DOCUMENTS

| | | | |
|---|---|---|---|
| 4,732,153 A * | 3/1988 | Phillips | A61B 5/14514 |
| | | | 422/68.1 |
| 8,684,900 B2 | 4/2014 | Tran | |
| 8,688,189 B2 | 4/2014 | Shennib | |
| 9,652,946 B2 | 5/2017 | Ramstein et al. | |
| 10,433,646 B1 * | 10/2019 | Schmidt | A47C 9/00 |
| 2002/0105436 A1 * | 8/2002 | Bell | G01K 7/245 |
| | | | 340/870.17 |
| 2002/0107436 A1 * | 8/2002 | Barton | A61B 5/0008 |
| | | | 600/382 |
| 2004/0077934 A1 * | 4/2004 | Massad | A61B 5/0205 |
| | | | 600/300 |
| 2005/0106713 A1 * | 5/2005 | Phan | B01L 3/502738 |
| | | | 435/287.2 |
| 2005/0190065 A1 * | 9/2005 | Ronnholm | A61M 21/00 |
| | | | 340/575 |
| 2007/0027388 A1 | 2/2007 | Chou | |
| 2008/0146890 A1 * | 6/2008 | LeBoeuf | A61B 5/4839 |
| | | | 600/300 |
| 2009/0143636 A1 * | 6/2009 | Mullen | A61B 5/0476 |
| | | | 600/26 |
| 2010/0125218 A1 * | 5/2010 | Haartsen | A61B 5/02438 |
| | | | 600/528 |
| 2011/0010014 A1 * | 1/2011 | Oexman | A47C 27/061 |
| | | | 700/276 |
| 2011/0295083 A1 * | 12/2011 | Doelling | A61B 5/103 |
| | | | 600/301 |
| 2013/0172691 A1 * | 7/2013 | Tran | A61B 8/488 |
| | | | 600/301 |
| 2014/0121557 A1 * | 5/2014 | Gannon | A61B 5/002 |
| | | | 600/549 |
| 2015/0087894 A1 * | 3/2015 | Rink | A61M 21/02 |
| | | | 600/28 |
| 2015/0351688 A1 * | 12/2015 | Just | A61B 5/681 |
| | | | 600/407 |
| 2016/0128488 A1 * | 5/2016 | Franceschetti | A47C 21/044 |
| | | | 5/421 |
| 2016/0217672 A1 * | 7/2016 | Yoon | A61B 5/4812 |
| 2017/0049397 A1 * | 2/2017 | Sun | G01K 7/427 |
| 2017/0258329 A1 * | 9/2017 | Marsh | G01J 5/0215 |
| 2018/0078732 A1 * | 3/2018 | Keshavan | A61B 5/4812 |
| 2018/0078735 A1 * | 3/2018 | Dalgleish | H04R 1/406 |
| 2018/0279952 A1 * | 10/2018 | Orron | A61B 5/02438 |
| 2019/0099009 A1 * | 4/2019 | Connor | A61B 5/0205 |
| 2019/0269883 A1 * | 9/2019 | Jung | A61B 5/4812 |
| 2022/0065710 A1 * | 3/2022 | Allen, Sr. | H04W 4/70 |

FOREIGN PATENT DOCUMENTS

| | | |
|---|---|---|
| JP | 6067065 B2 | 1/2017 |
| WO | PCT/US18/43722 | 7/2018 |
| WO | 2019023360 A2 | 1/2019 |

OTHER PUBLICATIONS

U.S. Appl. No. 16/049,759, US, Individual Wake-Up Alarm Patch, filed Jul. 30, 2018.
International Search Report for International Application No. PCT/US2018/043722, dated Jun. 5, 2019.
Written Opinion of the Searching Authority for International Application No. PCT/US2018/043722, dated Jun. 5, 2019.

* cited by examiner

USER COMFORT CONTROL SYSTEM HAVING NON-INVASIVE BIO-PATCH

CROSS-REFERENCE TO RELATED APPLICATION(S)

This application claims priority to U.S. Provisional Application No. 62/536,938 filed Jul. 25, 2017, entitled USER COMFORT CONTROL SYSTEM HAVING NON-INVASIVE BIO-PATCH, the disclosure of which is hereby expressly incorporated by reference herein in its respective entirety.

BACKGROUND

Field

The present disclosure relates to a wearable patch configured to support a user comfort system.

Description of the Related Art

Environmental conditions are important for comfort of people during various daily activities. For example, during daytime activities such as work, a proper range of temperature in a room is highly desirable. Similarly, during nighttime activities such as sleep, a proper range of temperature is also highly desirable for providing a more effective rest.

SUMMARY

In accordance with some teachings, the present disclosure relates to a wearable patch that includes a patch substrate configured to support a plurality of components, and to allow the patch to be attached to a skin of a user. The wearable patch further includes a sensor implemented at least partially within the patch substrate and configured to sense a biological condition of the skin. The wearable patch further includes a transmitter circuit in communication with the sensor and configured to transmit information representative of the sensed biological condition to a location external to the wearable patch.

In some embodiments, the biological condition can include a temperature of the skin or a perspiration level of the skin. In some embodiments, the patch substrate can include an adhesive layer configured to allow the wearable patch to stick to the skin of the user. The patch substrate can be dimensioned to be worn on, for example, an arm of the user or an earlobe of the user.

In some embodiments, the patch substrate can be configured to worn by the user when the user is sleeping. In some embodiments, the wearable patch can further include a controller configured to generate a control signal based on the sensed biological condition of the skin. The control signal can be configured to result in an adjustment of an environmental condition that affects sleeping comfort of the user.

In some implementations, the present disclosure relates to a method for adjusting a comfort level of a person. The method includes sensing, with a sensor of a wearable patch attached to a skin of the person, a biological condition of the skin. The method further includes transmitting information representative of the sensed biological condition to allow generation of a control signal based on the information.

In some embodiments, the method can further include attaching the wearable patch to the person prior to the sensing. In some embodiments, the method can further include generating the control signal. In some embodiments, the method can further include providing the control signal to a device implemented to provide comfort for the person, such that operation of the device is adjusted in response to the control signal.

In some embodiments, the device can be a bed having a temperature adjustment element. The temperature adjustment element can be configured to provide either or both of cooling and heating for the person based on the sensed biological condition of the skin. The biological condition can include a temperature of the skin or a perspiration level of the skin.

In some implementations, the present disclosure relates to a system for providing comfort for a person. The system includes a wearable patch configured to be attached to a skin of the person and sense a biological condition of the skin. The wearable patch is further configured to transmit information representative of the sensed biological condition. The system further includes a controller configured to receive the information and generate a control signal. The system further includes an adjustment element associated with a furniture item implemented to support and provide comfort for the person. The adjustment element is in communication with the controller and is configured to adjust a comfort level of the furniture item for the person in response to the control signal.

In some embodiments, the adjustment element can be configured as an accessory to the furniture item. In some embodiments, the adjustment element can be an integral part of the furniture item.

In some embodiments, the furniture item can be, for example, a bed. The adjustment element can be configured to provide either or both of cooling and heating for the person based on the sensed biological condition of the skin.

In some embodiments, the controller can be implemented as a part of the wearable patch. In some embodiments, the controller can be implemented as a dedicated device associated with the furniture item. In some embodiments, the controller can be implemented as a dedicated device associated with the adjustment element. In some embodiments, the controller can be implemented as an application software operating in a wireless device such as a smartphone.

In some embodiments, the controller can be further configured to allow an input from the person to provide feedback for effectiveness of the adjustment of the comfort level to thereby provide a personalized comfort setting for the person.

According to some implementations, the present disclosure relates to a kit for facilitating comfort of a person. The kit includes a plurality of wearable patches implemented in a packaged format, with each wearable patch including a patch substrate configured to support a plurality of components, and to allow the wearable patch to be attached to a skin of the person. Each wearable patch further includes a sensor implemented at least partially within the patch substrate and configured to sense a biological condition of the skin, and a transmitter circuit in communication with the sensor and configured to transmit information representative of the sensed biological condition. The kit further includes a printed instruction configured to facilitate use of the wearable patch on the person.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a

DETAILED DESCRIPTION OF SOME EMBODIMENTS

The headings provided herein, if any, are for convenience only and do not necessarily affect the scope or meaning of the claimed invention.

Disclosed are examples related to systems, methods and devices for providing enhanced level of comfort for users during daily activities such as sleeping on beds. As generally understood and experienced by many, a person can become uncomfortable during a sleeping period due to a number of reasons, even if the person begins sleeping in a condition that is "just right." For example, the person may set a thermostat to a selected setting for sleeping, wear a desired sleepwear for comfort, and cover himself/herself with a comforter (or decide to be not covered when warmer).

When that person sleeps, there may be changes in environmental conditions and/or changes in his/her body that result in the sleeping conditions being less comfortable. For example, a sleeping condition may change so that the person feels too warm, thereby resulting in discomfort and a sleep experience that is less than ideal.

Figure 1:
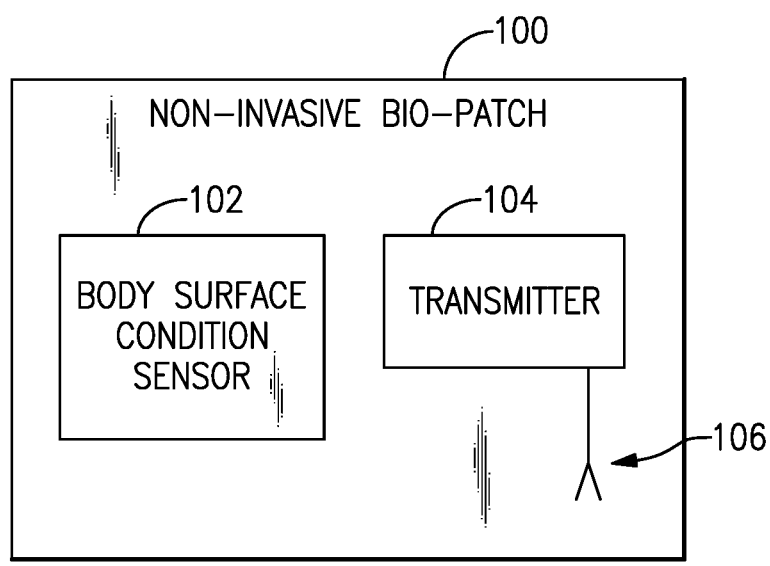
FIG. 1 depicts a non-invasive bio-patch device that can be worn by a person during activities such as sleep.

FIG. 1 depicts a non-invasive bio-patch device 100 that can be worn by a person during activities such as sleep. Although various examples are described herein in the context of sleep, it will be understood that one or more features of the present disclosure can also be utilized in other activities.

FIG. 1 shows that in some embodiments, the non-invasive bio-patch 100 can include body sensor such as a body surface condition sensor 102 and a transmitter 104 configured to transmit information about one or more body surface conditions sensed by the sensor 102. Such transmission of information can be supported by an antenna 106 in communication with the transmitter 104.

Figure 2:
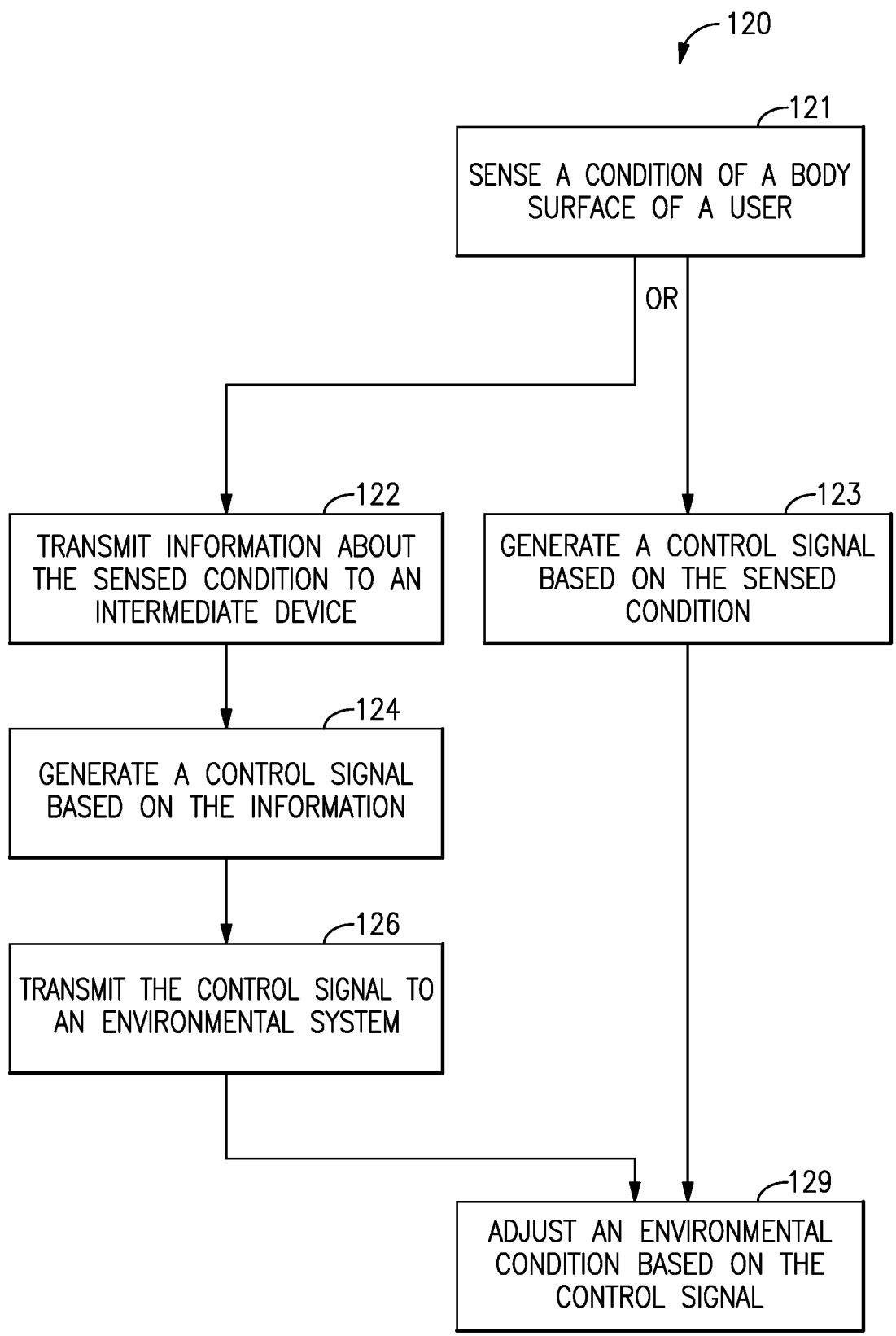
FIG. 2 shows a process that can be implemented by a system that includes the non-invasive bio-patch of FIG. 1.

FIG. 2 shows a process 120 that can be implemented by a system that includes the non-invasive bio-patch 100 of FIG. 1. In block 121, a condition of a body surface of a user can be sensed. In some embodiments, such sensing of the body surface condition can be achieved by the non-invasive bio-patch 100 of FIG. 1.

In FIG. 2, the foregoing sensed body surface condition can be utilized to adjust an environmental condition in block 129. For the purpose of description, it will be understood that an environmental condition can include, for example, air temperature, relative humidity of the air, lighting condition, condition of a bed, and/or any other condition that can impact the quality of sleep of the user. Such adjustment of the environmental condition based on the sensed body surface condition can be implemented in a number of ways.

For example, in some embodiments, a non-invasive bio-patch 100 of FIG. 1 can be configured to communicate the sensed body surface information directly with a device that effectuates the adjustment of the environmental condition.

Accordingly, in block 123, a control signal can be generated based on the sensed body surface condition, and such a control signal can be utilized to adjust the environmental condition (in block 129).

In another example, in some embodiments, an intermediate device can be utilized to provide control functionality between a non-invasive bio-patch 100 of FIG. 1 and a device that effectuates the adjustment of the environmental condition. In such a configuration, information about the sensed body surface condition can be transmitted by the non-invasive bio-patch 100 to the intermediate device in block 122. Based on such sensed body surface condition information, a control signal can be generated by the intermediate device in block 124. In block 126, the control signal can be transmitted by the intermediate device to the adjustment-effectuating-device to adjust the environmental condition (in block 129).

In some embodiments, a system as described herein can be configured to provide either or both of the control functionalities of FIG. 2.

Figure 3:
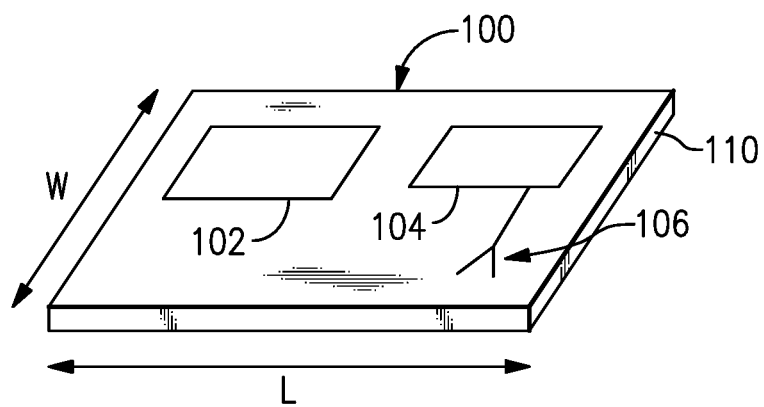
FIG. 3 shows that in some embodiments, a non-invasive bio-patch can have a generally rectangular shape.
Figure 4:
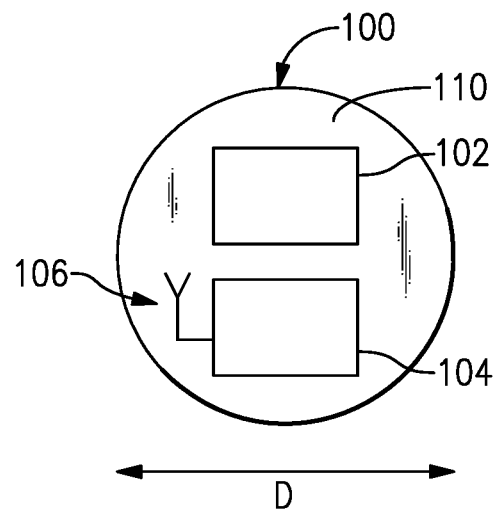
FIG. 4 shows that in some embodiments, a non-invasive bio-patch can have an elliptical shape, such as a circular shape.

FIGS. 3 and 4 show non-limiting examples of how a non-invasive bio-patch 100 can be implemented in different form factors. For example, FIG. 3 shows that in some embodiments, a non-invasive bio-patch 100 can have a generally rectangular shape with a length L and a width W. Such dimensions can be selected to, for example, allow application of the bio-patch 100 on an area of the user with sufficient space (e.g., on an arm). By way of examples, the length L can be 2 to 4 inches, and the width W can be 1 to 2 inches.

In another example, FIG. 4 shows that in some embodiments, a non-invasive bio-patch 100 can have an elliptical shape, such as a circular shape, with a diameter D. Such a dimension can be selected to, for example, allow application of the bio-patch 100 on a smaller area of the user that is more discreet and/or more sensitive to body surface condition (e.g., on an earlobe). By way of an example, the diameter D can be ⅛ to ½ inch.

It will be understood that a non-invasive bio-patch 100 having one or more features as described herein can be implemented with other shapes.

In the examples of FIGS. 3 and 4, each non-invasive bio-patch 100 can include a patch substrate 110 configured to provide wearable functionality and to support a number of components. Examples related to such wearable functionality and support functionality can be found in U.S. Pat. No. 9,133,024 titled PERSONAL DIAGNOSTIC DEVICES INCLUDING RELATED METHODS AND SYSTEMS, which is expressly incorporated by reference in its entirely, and its disclosure is to be considered part of the specification of the present application.

In the examples of FIGS. 3 and 4, each non-invasive bio-patch 100 is shown to include a body surface condition sensor 102, a transmitter 104, and an antenna 106, similar to the example of FIG. 1. In some embodiments, at least the transmitter portion of the bio-patch 100 can be include an RFID (radio-frequency identification) circuitry configured to support transfer of information between the bio-patch 100 and a device external to the bio-patch 100.

Figure 5:
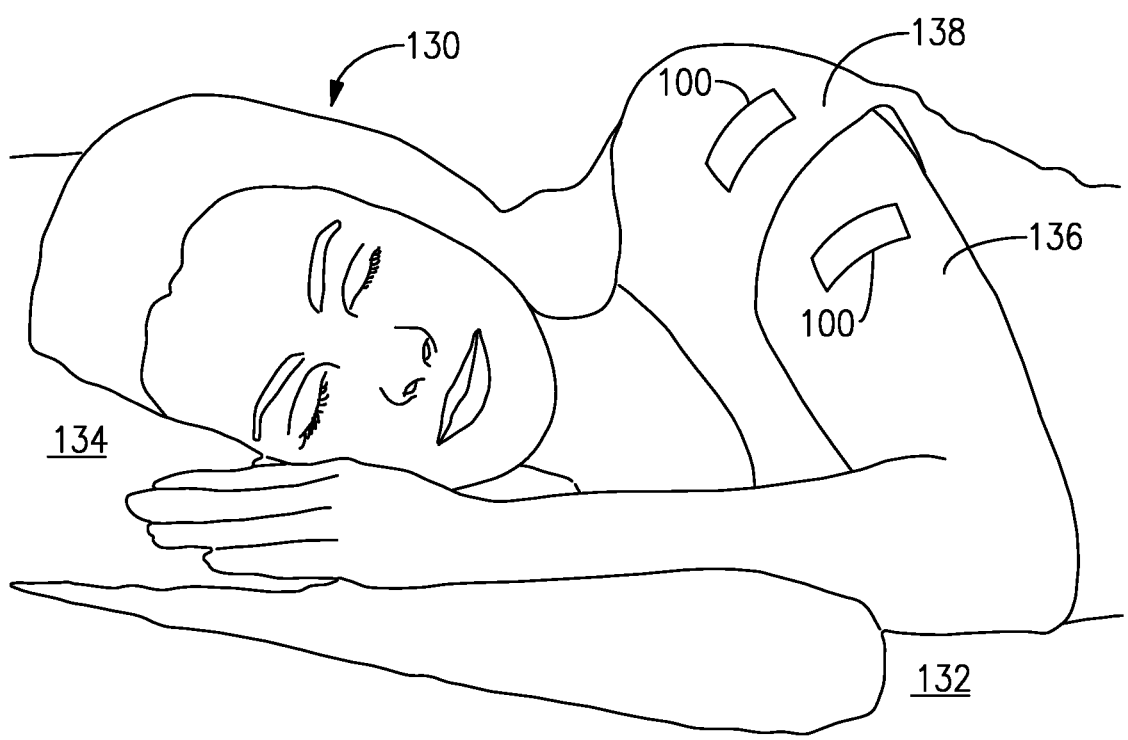
FIG. 5 shows a person sleeping on a bed and wearing a non-invasive bio-patch having one or more features as described herein.

FIG. 5 shows a person 130 sleeping on a bed 132 with her head supported by a pillow 134. FIG. 5 further shows that such a sleeping person can wear a non-invasive bio-patch 100 having one or more features as described herein at one or more locations. For example, a non-invasive bio-patch 100 can be configured to be worn on an exposed skin of an arm 136. In another example, a non-invasive bio-patch 100 can be configured to be worn on a surface of a clothing item 138 that is sufficiently close to the skin. In some embodiments, the non-invasive bio-patch(es) 100 worn by the user 130 can have a larger form factor such as in the example of FIG. 3.

Figure 6A:
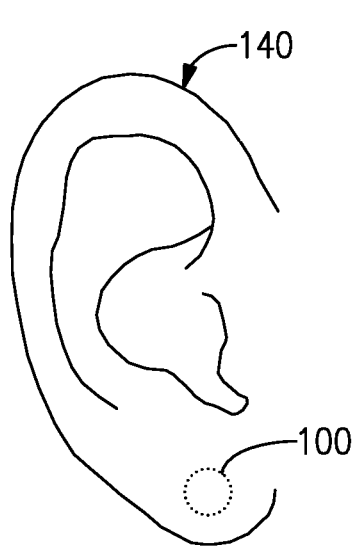
FIGS. 6A and 6B show that in some embodiments, a non-invasive bio-patch having one or more features as described herein can be configured to be worn on a smaller portion of a user.
Figure 6B:
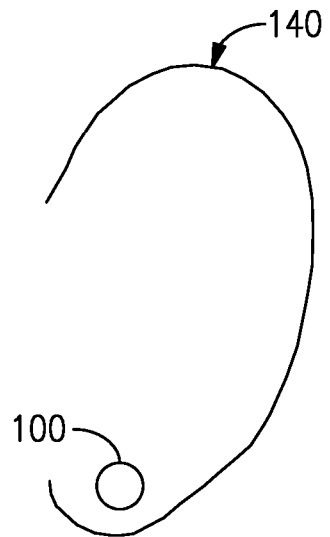

FIGS. 6A and 6B show that in some embodiments, a non-invasive bio-patch 100 having one or more features as described herein can be configured to be worn on a smaller portion of a user (e.g., the sleeping person 130 in FIG. 5). For example, the non-invasive bio-patch 100 is shown to be worn on the surface of an earlobe on the back side of an ear 140. FIG. 6A depicts the front side (visible side) of the ear 140, and FIG. 6B depicts the back side (generally hidden side) of the ear 140.

It will be understood that a non-invasive bio-patch 100 having one or more features as described herein can be worn at other parts of a user. Such patch application locations can be based on, for example, whether a location is likely covered or exposed during sleep, whether a location is likely be impacted by various movements during sleep, whether a location provides an appropriate indication of change in body temperature, or some combination thereof.

In some embodiments, a single non-invasive bio-patch 100 having one or more features as described herein can be applied and utilized as described herein. In some embodiments, a plurality of non-invasive bio-patches 100 having one or more features as described herein can be applied and utilized as described herein. In the latter example, sensed body condition information from the non-invasive bio-patches 100 can be at least partially integrated to effectuate change(s) in one or more environmental conditions that affect sleep comfort of the user.

Figure 7:
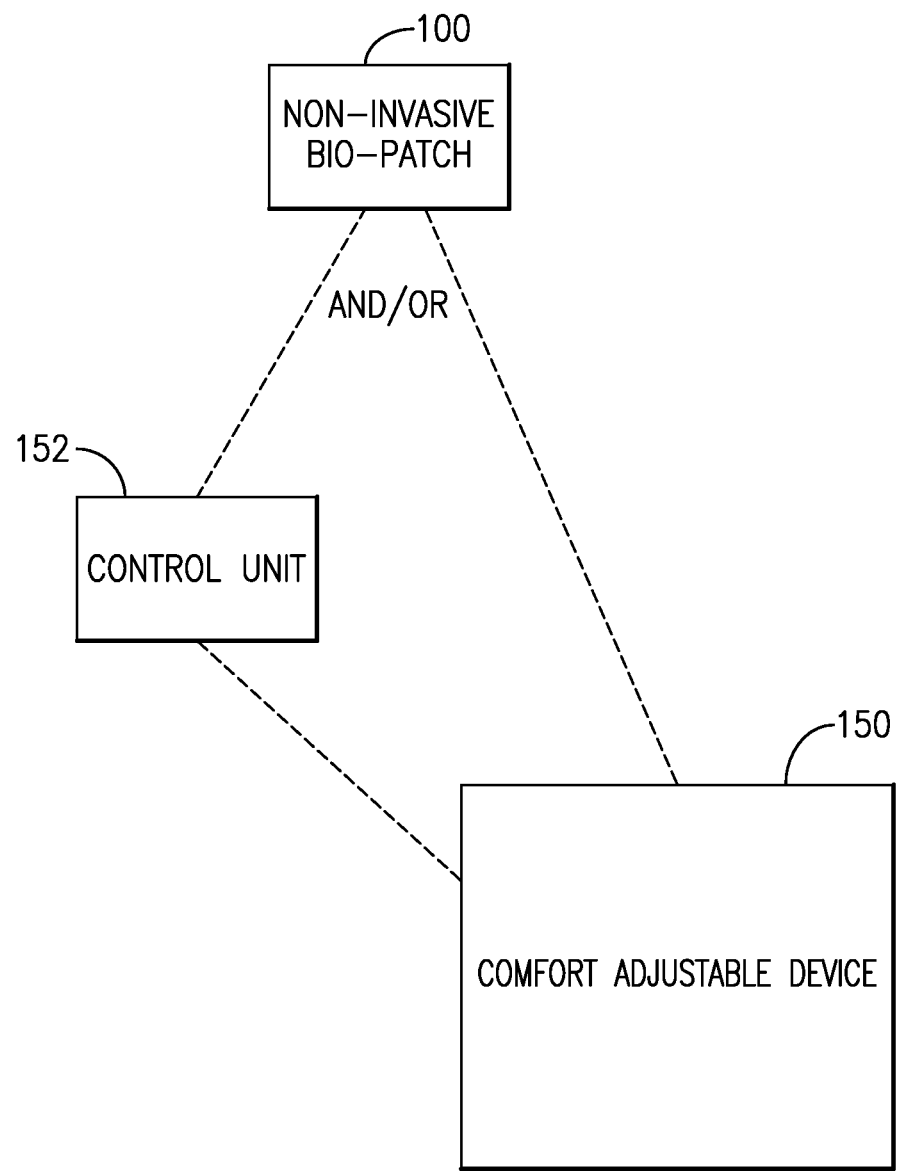
FIG. 7 depicts a block diagram of a system that can include a non-invasive bio-patch having one or more features as described herein.

FIG. 7 depicts a block diagram of a system that can include a non-invasive bio-patch 100 having one or more features as described herein. In some embodiments, such a system can be configured to perform the process(es) described herein in reference to FIG. 2.

In the example of FIG. 7, the bio-patch 100 can be configured to communicate directly with a device 150 having comfort adjustability. Examples related to such a comfort adjustable device are described in reference to FIGS. 8 and 9. In some embodiments, either or both of the bio-patch 100 and the comfort adjustable device 150 can include control circuitry that allows control of the comfort adjustable device 150 based on sensed information obtained by the bio-patch 100.

FIG. 7 further shows that in some embodiments, a separate control unit 152 can be provided to facilitate control of the comfort adjustable device 150 based on sensed information obtained by the bio-patch 100. For example, the bio-patch 100 and the separate control unit 152 can be configured to allow transfer of sensed information from the bio-patch 100 to the separate control unit 152. Based on such sensed information, the separate control unit 152 can generate and provide to the comfort adjustable device 150 a control signal to facilitate an adjustment of the comfort adjustable device 150.

In some embodiments, a system having one or more features as described herein can be configured to provide either or both of the foregoing control functionalities. It will be understood that a non-invasive bio-patch 100 having one or more features as described herein can be utilized to adjust a comfort adjustable device 150 with other control configurations.

Figure 8:
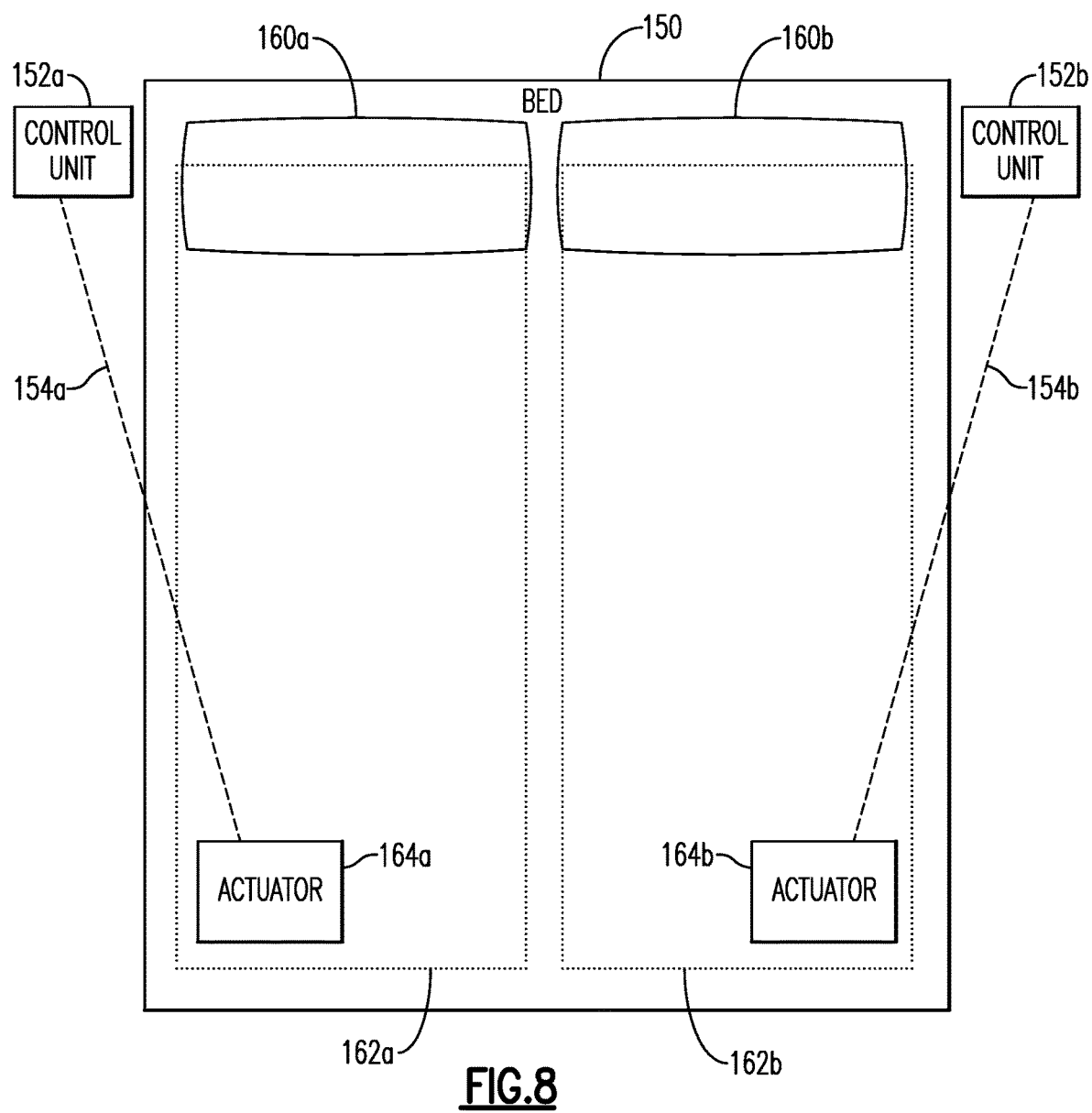
FIG. 8 shows that in some embodiments, a comfort adjustable device of the system of FIG. 7 can be a bed.

FIG. 8 shows that in some embodiments, the comfort adjustable device 150 of the system of FIG. 7 can be a bed 150 or an accessory associated with a bed. For the purpose of description, it will be assumed that the comfort adjustable device 150 is a bed having adjustability; however, it will be understood that one or more features of the present disclosure can also be implemented with an adjustable accessory that may or may not be integrated with a bed. A bed having one or more features of the present disclosure is described in the context of the example sleeping activity of FIGS. 5 and 6.

In the example of FIG. 8, the bed 150 is depicted as a being configured to accommodate two sleeping persons; however, it will be understood that a bed having one or more features as described herein can also be configured for other numbers of sleeping persons, including a single bed for one person.

In the example of FIG. 8, the bed 150 is depicted as a being configured to provide separate comfort adjustability for each sleeper; however, it will be understood that a bed having one or more features as described herein can also be configured to provide a common comfort adjustability for both sleepers. In such an example, the bed can be in communication with a common controller.

Referring to the example of FIG. 8, the bed 150 is shown to include a first adjustment element 162a for providing a first sleeper (not shown, but assumed to be wearing a first bio-patch) with comfort adjustability. Such a first adjustment element can be controlled by a first control unit 152a through a first communication link 154a (e.g., a wireless or wired link). More particularly, a first actuator 164a of the first adjustment element 162a can be configured to receive a control signal from the first control unit 152a, and in response, actuate the first adjustment element 162a to provide a desired comfort adjustment.

Similarly, the bed 150 is shown to include a second adjustment element 162b for providing a second sleeper (not shown, but assumed to be wearing a second bio-patch) with comfort adjustability. Such a second adjustment element can be controlled by a second control unit 152b through a second communication link 154b (e.g., a wireless or wired link). More particularly, a second actuator 164b of the second adjustment element 162b can be configured to receive a control signal from the second control unit 152b, and in response, actuate the second adjustment element 162b to provide a desired comfort adjustment.

In some embodiments, each of the first and second adjustment elements 162a, 162b can be configured in a number of different ways to provide comfort adjustment of one or more sleeping conditions. For example, an adjustment element having one or more features as described herein can be configured to change the temperature of some or all of a sleeping surface of a respective sleeper. Such a temperature-changing functionality can include either or both of heating and cooling functionalities.

For example, an adjustment element can include a heating element having an array of wires heated by application of electricity and controlled by a signal from a corresponding control unit. In such a configuration, the heating element can be turned on at a selected level and/or be operated for a selected duration, based on the control signal. For example, suppose that a control signal indicates that the sleeper's body surface temperature (at the area where the bio-patch is applied) is cooler than some threshold value. Then, the heating element can be turned on at a selected level (e.g., low setting if the sensed surface temperature is below the threshold value by a small amount) for a selected period, or until an updated control signal is received (e.g., a control signal to turn off the heating element based on a sensed surface temperature exceeding the threshold value).

In some situations, sleepers may prefer to not utilize electrical current close to their bodies for various reasons. In some embodiments, an adjustment element having one or more features as described herein can be configured to provide heating and/or cooling functionalities utilizing non-electrical techniques.

Figure 9:
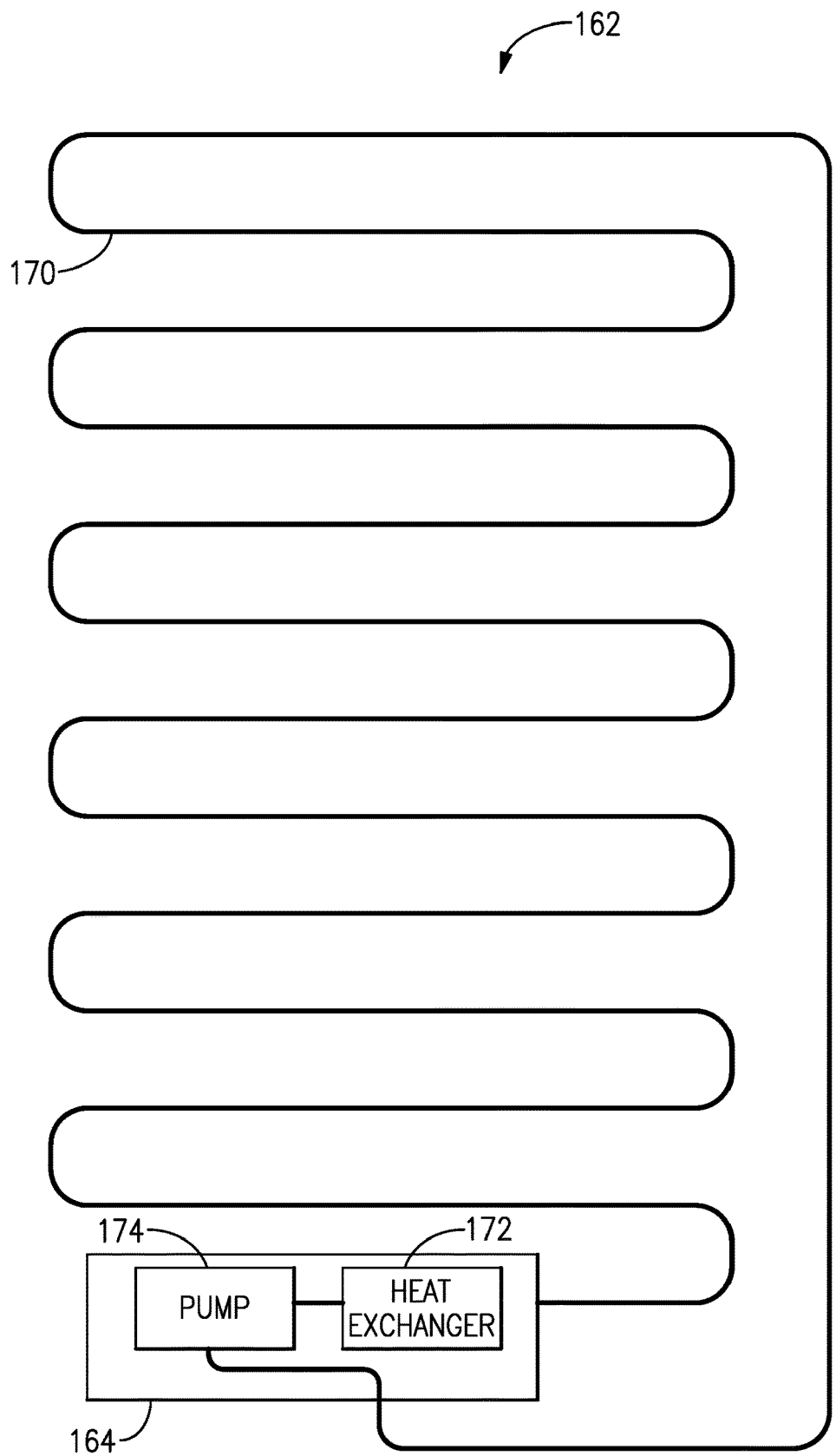
FIG. 9 depicts an adjustment element configured to circulate liquid to provide either or both of heating and cooling functionalities for the bed of FIG. 7.

For example, FIG. 9 depicts an adjustment element 162 configured to circulate liquid to provide either or both of heating and cooling functionalities. In some embodiments, such an adjustment element can be implemented for each of the first and second adjustment elements 162a, 162b in the example of FIG. 8.

In the example of FIG. 9, the adjustment element 162 can include a closed-loop of liquid path having, for example, a tubing 170 (e.g., ⅛ to ¼ diameter tubing) configured to flow therein a liquid such as water. Such a closed loop of liquid path can include an actuator 164 having a heat exchanger 172 and a pump 174. The heat exchanger 174 can be configured to remove heat from the circulating liquid (e.g., water) when cooling is desired, to add heat to the circulating liquid when heating is desired, or to be turned off if a change in temperature is not desired. The pump 174 can be configured to operate at one or more different pumping rates when a change in temperature is desired, or to be turned off if a change in temperature is not desired.

For example, if a relatively large amount of heating is desired in response to a control signal (indicative of a relatively large decrease in sensed surface temperature), the heat exchanger 172 can be operated at a higher setting to add heat to the circulating liquid, and the pump 174 can also be operated at a higher setting. In another example, if a relatively small amount of cooling is desired in response to a control signal (indicative of a relatively small increase in sensed surface temperature), the heat exchanger 172 can be operated at a lower setting to remove heat from the circulating liquid, and the pump 174 can also be operated at a lower setting. In yet another example, if a change in temperature of the liquid is not desired in response to a control signal (indicative of an approximately uniform sensed surface temperature), each of the heat exchanger 172 and the pump 174 can be turned off or be in a stand-by mode.

Based on the foregoing examples, one can see that a number of other operating configurations can be implemented for the heat exchanger 172 (with one or more on-level settings) and the pump 174 (with one or more on-level settings).

As described herein, use of a bio-patch can enhance physiological activities such as sleep (e.g., as described in reference to FIGS. 5, 6, 8 and 9. FIGS. 10-15 show examples of how bio-patches can be packaged for easier use by a user, as well as how a bio-patch can be configured to provide one or more features as described herein.

Figure 10:
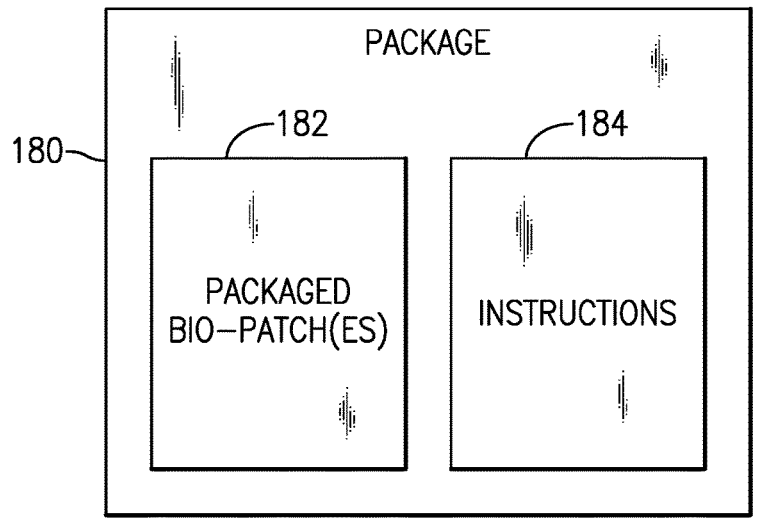
FIG. 10 shows that in some embodiments, one or more bio-patches having one or more features as described herein can be in a packaged format for easier use by a user.

FIG. 10 shows that in some embodiments, one or more bio-patches having one or more features as described herein can be provided in a packaged format 182 for easier use by a user. Such a packaged format of bio-patch(es) can be included in, for example, a packaged product 180. In some embodiments, the packaged product 180 can also include an instruction 184 such as a printed instruction. Such an instruction can provide information on, for example, proper and/or recommended application of the included bio-patch(es).

Figure 11:
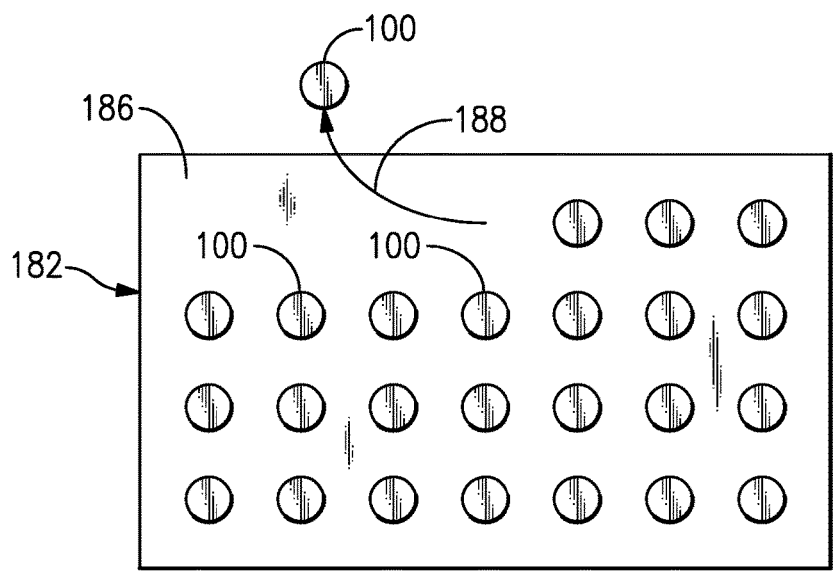
FIG. 11 shows an example of a packaged format having a support sheet with a plurality of bio-patches secured thereto.

FIG. 11 shows an example of a packaged format 182 having a support sheet 186 with a plurality of bio-patches 100 secured thereto. Such number of bio-patches can allow a user to remove (arrow 188) a bio-patch 100 from the support sheet 186 for use during a sleeping period. For example, one bio-patch can be utilized each night. In some applications, such use of bio-patches can be performed for an unspecified number of days, only as needed or desired, for a specified number of days to build a sleeping profile of the user, or any combination thereof. Examples related to such a sleeping profile being obtained using the bio-patches are described herein in greater detail.

Figure 12:
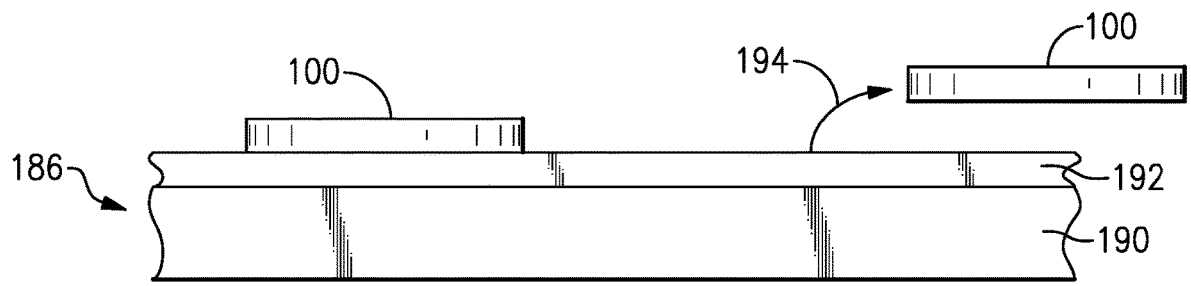
FIG. 12 shows an enlarged side sectional view of an example support sheet that can be utilized to hold, until removal, a plurality of bio-patches, similar to the example of FIG. 11.

FIG. 12 shows an enlarged side sectional view of an example support sheet 186 that can be utilized to hold (until removal) a plurality of bio-patches, similar to the example of FIG. 11. In some embodiments, the support sheet 186 can include a base layer 190 (e.g., paper, plastic, etc.) and a release layer 192. The release layer 192 can be secured to the base layer 190, and be configured to securely hold the bio-patches 100 thereon during transport and storage phases. Assuming that a bio-patch includes an adhesive layer for application onto the skin of a user, the release layer can further be configured to allow the bio-patch to be removed (e.g., peeled off) cleanly for application onto the user. In the example of FIG. 12, such removal of the bio-patch 100 from the release layer 192 is depicted as an arrow 194.

Figure 13:
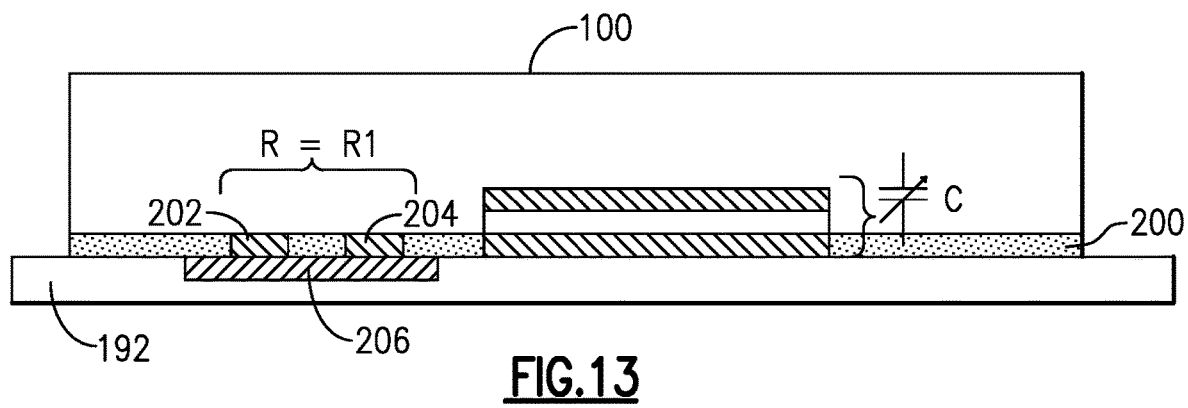
FIG. 13 shows a side sectional view of an example bio-patch having a pair of surface contacts configured to allow measurement of resistance therebetween, and an adhesive layer configured to allow the bio-patch to be removed from a release layer for application onto a skin of a user.
Figure 14:
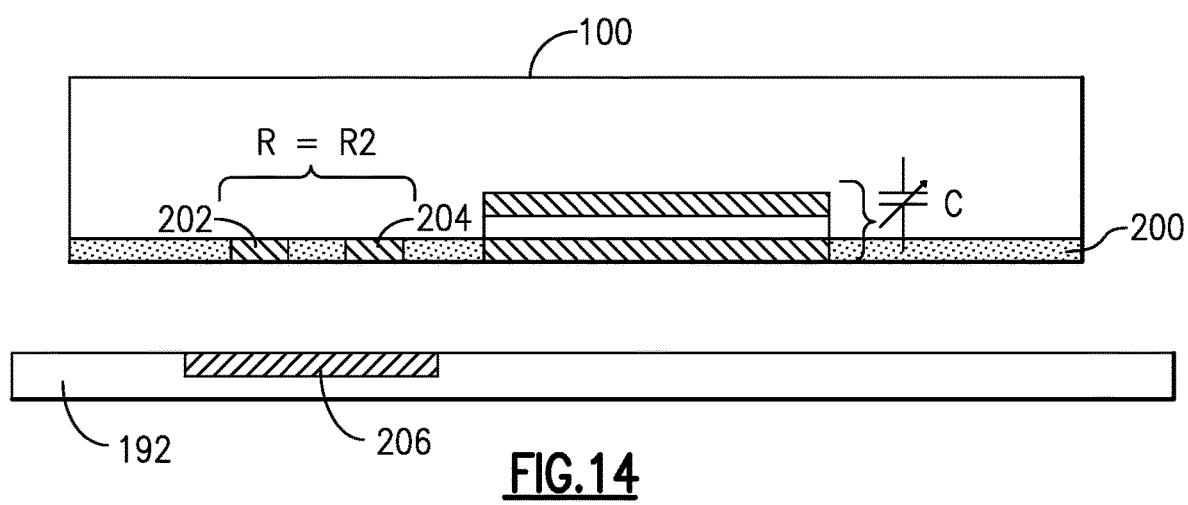
FIG. 14 shows the bio-patch of FIG. 13 being removed from the release layer, such that the pair of contacts are no longer in physical contact with a conductive portion of the release layer.
Figure 15:
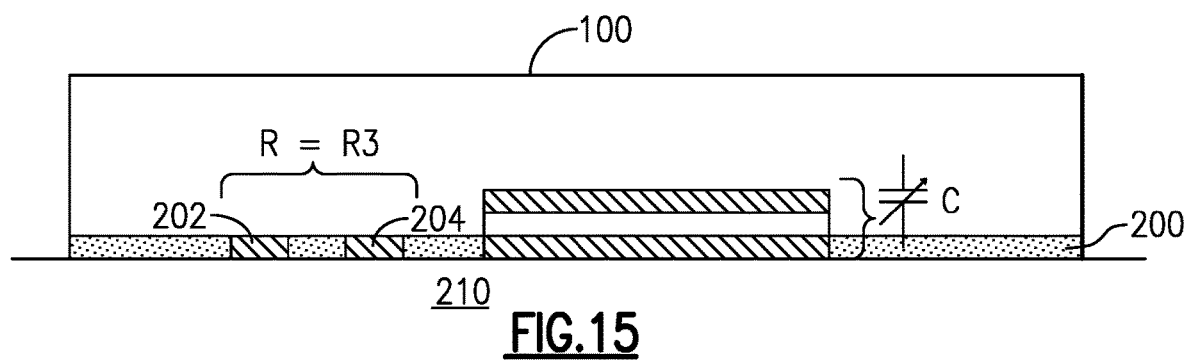
FIG. 15 shows the bio-patch of FIG. 13 attached to a surface of a skin of a user with the adhesive layer, such that the pair of contacts can be utilized to measure the resistance of the surface of the skin between the pair of contacts.

In some embodiments, it may be desirable to have a bio-patch to be in an inactive state before use, and an active state during use. FIGS. 13-15 show an example of how a bio-patch 100 can be configured to provide such inactive and active states.

FIG. 13 shows a side sectional view of an example bio-patch 100 having one or more features as described herein. In some embodiments, the bio-patch 100 can include a pair of surface contacts 202, 204 configured to allow measurement of resistance therebetween. Such surface contacts can co-exist with an adhesive layer 200 that is configured to allow the bio-patch 100 to be removed from a release layer 192 for application onto the skin of a user.

The bio-patch 100 can further include an activation circuit coupled to the pair of contacts 202, 204 and configured to put the bio-patch 100 in an inactive state when the resistance R has a first value R1 between the pair of contacts 202, 204. In the example of FIG. 13, the bio-patch 100 is still secured on the release layer 192 that includes a conductive portion 206 under the pair of contacts 202, 204. Accordingly, the first resistance value R1 will be approximately zero or have a very low value; and the inactive state can be based on such a zero or very low resistance value.

FIG. 14 shows the bio-patch 100 being removed from the release layer 192, such that the pair of contacts 202, 204 are no longer in physical contact with the conductive portion 206. Accordingly, a second resistance value of R2 exists between the pair of contacts 202, 204, and such a second resistance value will be approximately infinite or very high. In some embodiments, such an infinite or very high resistance value can be utilized to activate the bio-patch 100.

FIG. 15 shows the bio-patch 100 attached to a surface of a skin 210 of a user with the adhesive layer 200. Accordingly, the pair of contacts 202, 204 can be utilized to measure the resistance (R3) of the surface of the skin 210 between the pair of contacts 202, 204. In some embodiments, such a resistance value (R3) can be utilized in a number of ways. For example, the resistance value R3 can be utilized to activate the bio-patch 100 (instead of the activation of FIG. 14), as a secondary activation or for some other preparation process, and/or for sensing of a condition (e.g., perspiration level) associated with the skin 210 of the user.

In the examples of FIGS. 13-15, the bio-patch 100 is shown to include a capacitor having a capacitance C. Such a capacitor can be configured to provide temperature dependence, such that variation in the capacitance C can be utilized to determine variation in temperature of the skin (210 in FIG. 15). To measure such variation in capacitance/temperature, the variable capacitor can be configured as a sheet capacitor, with one electrode positioned to be in thermal contact with the skin 210 (either directly or through another layer).

In some embodiments, the variable capacitor and the circuit for determining the corresponding temperature variation can be parts of the body surface condition sensor 102 as described herein in reference to FIGS. 1, 3 and 4.

It will be understood that other circuits and methods can be utilized to activate a bio-sensor and/or to perform one or more surface condition measurements.

Figure 16:
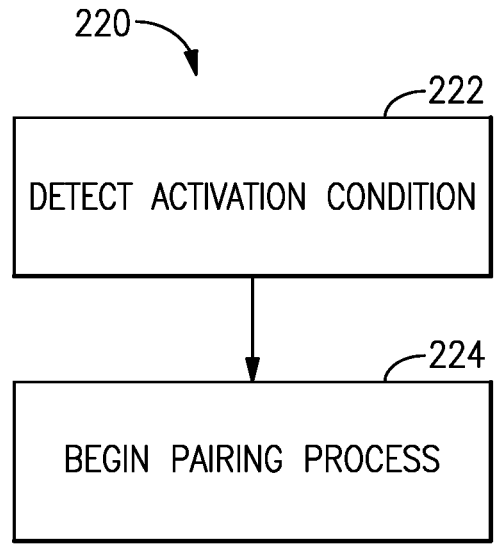
FIG. 16 shows a process that can be implemented in a bio-patch such as the example bio-patch of FIG. 13.
Figure 17:
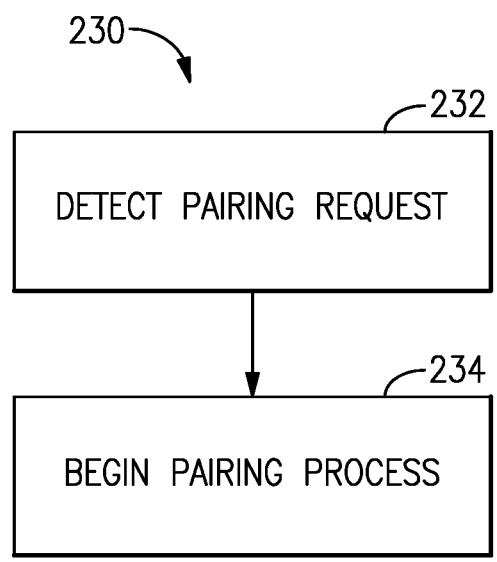
FIG. 17 shows a process that can be implemented in a controller associated with the bio-patch of FIG. 16.

As described herein in reference to FIGS. 10-15, it may be desirable to activate a bio-patch at an appropriate time (e.g., when removed from a release layer or when applied to the skin of a user). In some embodiments, such an activation can include a hand-shake pairing process between the bio-patch and a control unit (e.g., 152 in FIGS. 7 and 8). FIGS. 16 and 17 show examples of processes that can be implemented in the bio-patch and the control unit, respectively, to achieve such a hand-shake pairing process.

FIG. 16 shows a process 220 that can be implemented in the bio-patch. In block 222, an activation condition can be detected (e.g., as in the examples of FIGS. 13-15). In block 224, a pairing process can be initiated.

FIG. 17 shows a process 230 that can be implemented in the controller. In block 232, a pairing request can be detected (e.g., from a bio-patch, as a result of block 224). In block 234, a pairing process can be carried out with the bio-patch.

In the examples of FIGS. 16 and 17, the bio-patch can be configured to be able to detect an activation condition by itself. However, in some embodiments, a bio-patch can include an RFID circuitry that remains unpowered until interrogated by an external device such as a control unit. For such a configuration of the bio-patch, some or all of the process 220 of FIG. 16 can be triggered and performed upon an interrogation by the control unit.

In some embodiments, and as described herein, a control unit can be utilized to receive sensed information, such as skin temperature and/or perspiration level, from a bio-patch and generate a control signal for effectuating a comfort adjustment in a device such as a bed. Such a control unit can be implemented in a number of different ways.

For example, a control unit can be a dedicated device configured for operation with a specific bed or a type of bed. Such a dedicated device can generate control signals compatible with and understood by the corresponding bed. Alternatively, a control unit can be based on a more common standard that is compatible and understood by a corresponding bed.

On the sensed information side, a control unit can be configured for operation with a corresponding bio-patch utilizing a signal format compatible and understood by both. Similar to the control signal side (for controlling a bed), such a signal format can be specific for the bio-patch, or be based on a more common standard.

In another example, a control unit can be an application software (also referred to as an app) running on a device such as a smartphone. Similar to the dedicated device described above, the application software can be configured to receive and understand sensed information from a bio-patch, and to generate a control signal that is understood by a corresponding bed. The sensed information can have a format specific for the bio-patch, or be based on a more common standard. Similarly, the control signal can have a format specific for the bed, or be based on a more common standard.

In some embodiments, a control unit can further be configured to provide a calibration functionality. Such a calibration functionality can allow the resulting control signals to provide more personalized comfort settings.

Figure 18:
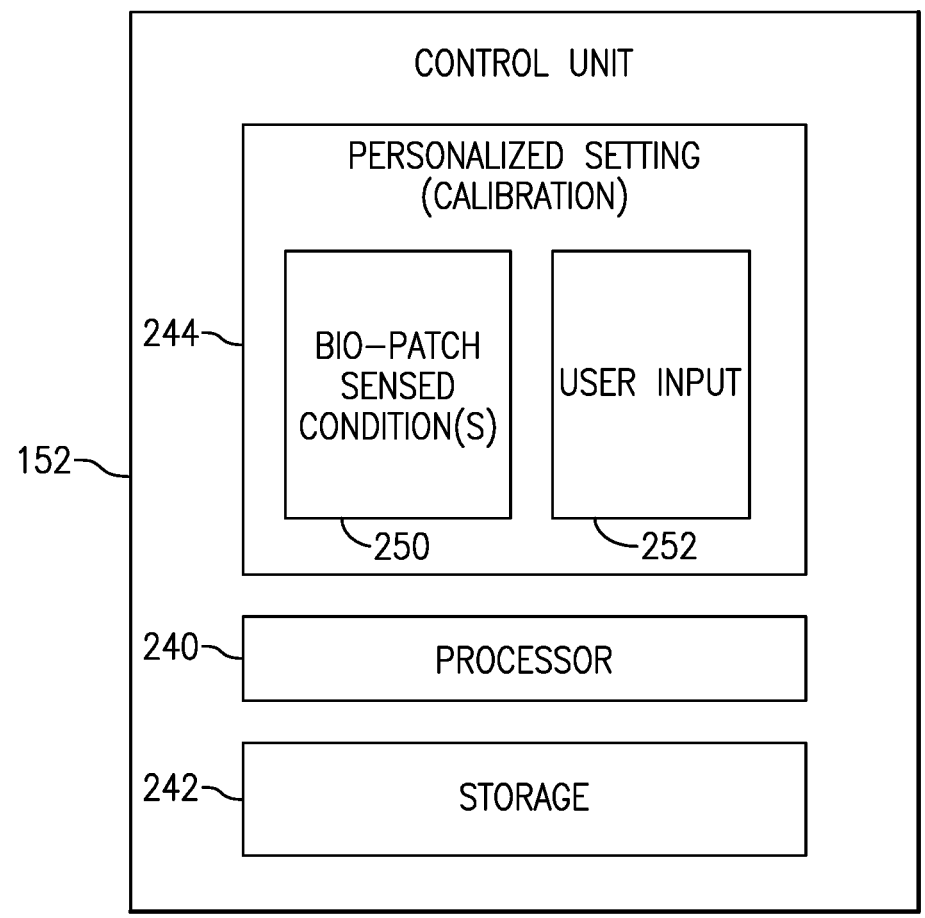
FIG. 18 depicts a control unit that includes a calibration component that can provide a personalized setting.

FIG. 18 depicts a control unit 152 that includes a calibration component 244 that can provide a personalized setting. Such a calibration component can be based on sensed condition information obtained from a bio-patch (indicated as 250), and a user input (indicated as 252).

By way of examples, suppose that during an initial use, a sensed condition information indicates that the skin temperature is higher than some pre-selected level. Based such input, the control unit 152 generates an initial control signal to provide an initial cooling adjustment for the user. However, because of physiological variations among different persons, the initial cooling adjustment may be too large (and thereby result in the user feeling cold) or too small (and thereby resulting in the user still feeling too warm).

As shown in the example of FIG. 18, the user input component 252 can be configured to interact with the user (e.g., the following day after the initial use of the bio-patch) and obtain a feedback. For example, the user can be asked if the cooling adjustment was too much, not enough, or appropriate; and the user's input can be stored. If the user input indicates that the cooling adjustment was too much, and another high skin temperature (by a similar amount) is sensed, an adjusted control signal can be generated based on the stored user input, so that the resulting cooling adjustment is less than the initial cooling adjustment. In some embodiments, one or more additional feedback cycles can be implemented with user inputs to further tune the comfort settings for the user.

In the foregoing example, the user input scheme includes relatively coarse adjustment inputs. It will be understood that finer granularity can be provided in such feedback inputs. For example, the user input component 252 can be configured to have the user rate "too much cooling" on a scale (e.g., 1 to 5, with 5 being the highest cooling adjustment). Based on such finer granularity input information, a control signal with corresponding granularity can be generated.

It will also be understood that a number of variables can be taken into account to provide improved personalized comfort settings. For example, a personalized comfort setting can be obtained for each of different seasons (e.g., winter, spring, summer and autumn). Depending on factors such as a particular user's physiology, frequency of use, feedback participation level, a desired set of personalized comfort setting can be obtained relatively quickly (e.g., about 3 to 4 nights).

As further shown in the example of FIG. 18, the control unit 152 can include a processor 240; and such a processor can provide and/or facilitate some or all of the foregoing control and calibration functionalities. The control unit 152 can further include a memory or storage component 242 (e.g., a non-transitory computer readable medium); and such a storage component can store information such as initial settings, user feedback inputs, etc.

Figure 19:
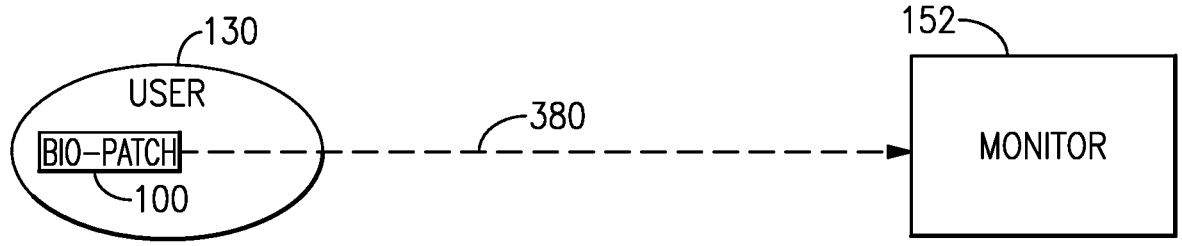
FIG. 19 shows an example of a communication functionality that can be implemented for a bio-patch.

As described herein, a patch having one or more features as described herein can include a communication component to facilitate transmission of information such as sensor data. FIG. 19 shows an example of a system that can be implemented to utilize such a communication functionality. For example, a patch 100 having one or more features as described herein is shown to be worn by a user 130. Information transmitted (e.g., in a wireless manner) is depicted as 380, and such information can be received by a monitor 152 (also referred to herein as a control unit). Such a monitor can include a receiver circuit configured to process the received signal from the patch 100. The monitor 152 can further include a processor to support various functionalities as described herein.

Figure 20:
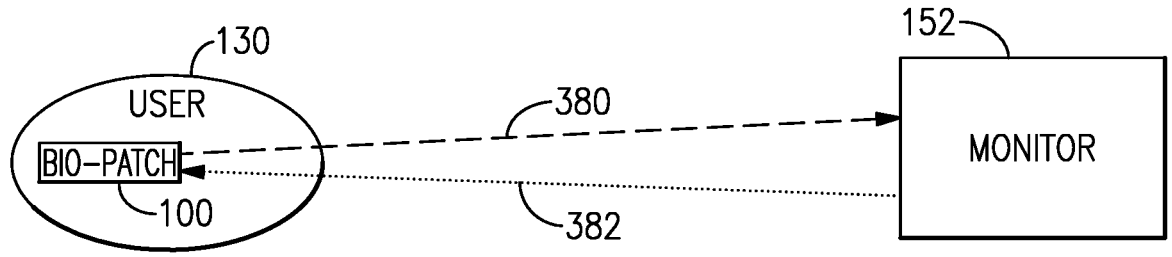
FIG. 20 shows an example of a communication functionality in which a bio-patch can include transmit and receive capabilities.

In some embodiments, a patch having one or more features as described herein can also include a receiver circuit to allow the patch to receive information such as instructions, diagnostics, etc. Accordingly, FIG. 20 shows an example of a system that can be implemented to utilize such transmit and receive functionalities. For example, a patch 100 having one or more features as described herein is shown to be worn by a user 130. Information transmitted (e.g., in a wireless manner) is depicted as 380, and such information can be received and processed by a monitor 152, similar to the example of FIG. 19.

In the example of FIG. 20, the patch 100 can also receive information (indicated as 382). Such received information can be achieved in a wireless mode, a wire mode, or any combination thereof. Although such information is depicted as being provided by the monitor 152, it will be understood that information provided to the patch 100 may or may not be from the same component (e.g., monitor 152 in FIG. 20).

Figure 21:
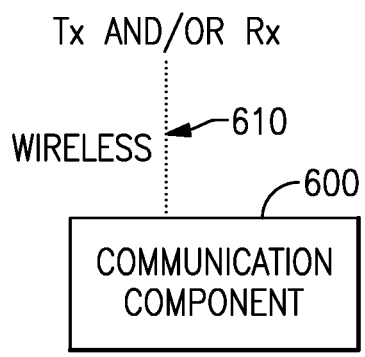
FIG. 21 shows that in some embodiments, a bio-patch can be configured to communicate with another device in a wireless manner.
Figure 22:
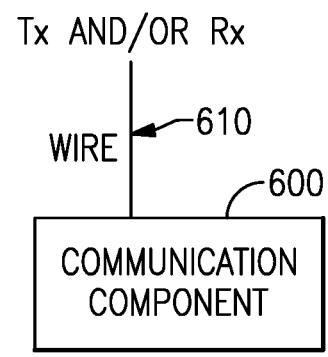
FIG. 22 shows that in some embodiments, a bio-patch can be configured to communicate with another device through a wire.

FIGS. 21-25 show examples of communications and/or system functionalities that can be implemented in a system having one or more patches as described herein. For example, FIGS. 21 and 22 show that in some embodiments, a communication component 600 (e.g., 104 in FIG. 1) of a patch can be configured to provide a wireless communication (depicted as 610 in FIG. 21) with an external device, a wired communication (depicted as 610 in FIG. 22) with an external device, or some combination thereof. For the purpose of description of FIGS. 21 and 22, an external device can be another patch, a non-patch device, etc.

In some embodiments, in each of the examples of FIGS. 21 and 22, the wireless and/or wired communication link 610 can include a transmit (Tx) functionality (relative to the corresponding patch), a receive (Rx) functionality, or any combination thereof.

Figure 23:
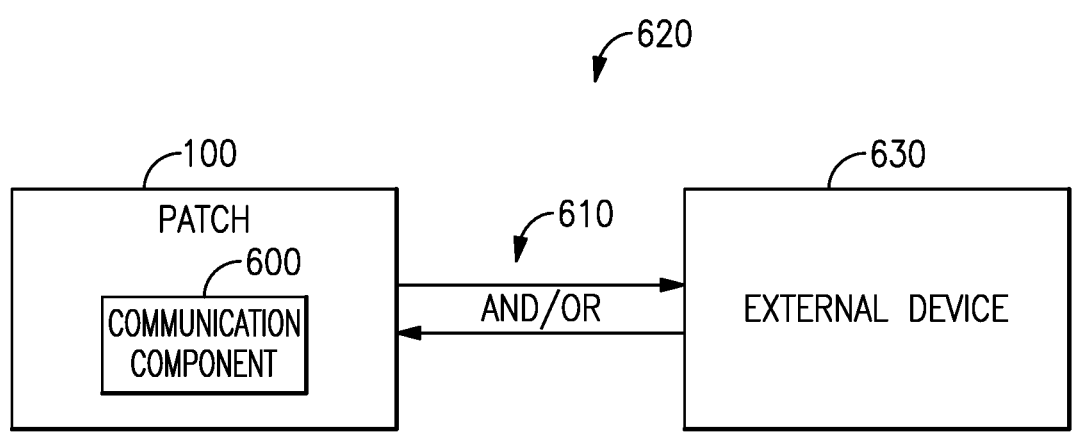
FIG. 23 shows that in some embodiments, a bio-patch and an external device can be in a system and communicate with each other.

FIG. 23 shows a system 620 that can be formed with one or more patches 100 as described herein, and an external device 630. For the purpose of description of FIG. 23, it will be understood that the external device 630 is relative to the patch 100. Thus, if the external device 630 is another patch, then the patch 100 shown in FIG. 23 can be considered to be external to the other patch (630). As described in reference to FIGS. 21 and 22, it will be understood that the external device 630 can be a patch that may or may not be similar to the patch 100.

In the example of FIG. 23, the patch 100 is shown to include a communication component similar to the examples of FIGS. 21 and 22. Accordingly, the communication between the patch 100 and the external device 630 can include transmit and/or receive portions.

Figure 24:
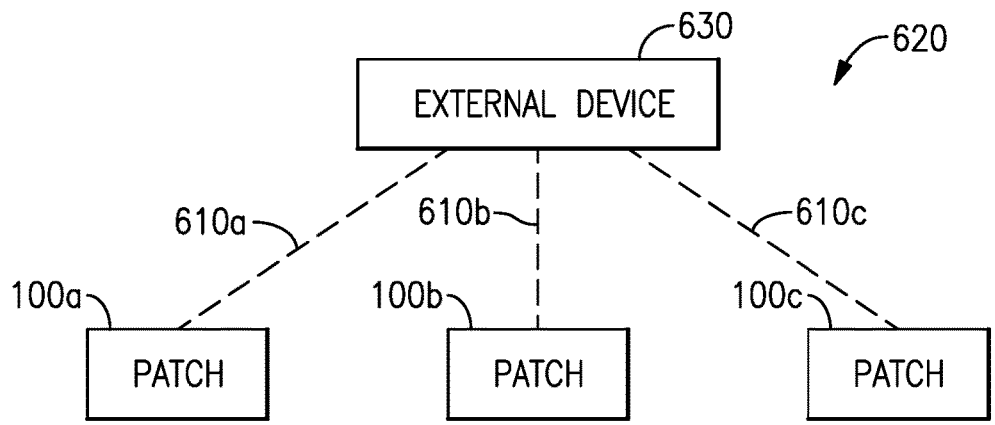
FIG. 24 shows that in some embodiments, the system of FIG. 23 can include a plurality of patches that communicate with a common external device.

FIG. 24 shows that in some embodiments, the system 620 of FIG. 23 can include a plurality of patches 100 that communicate with a common external device. For example, a system 620 of FIG. 24 is shown to include a plurality of patches 100a, 100b, 100c and an external device 630. More particularly, the first patch 100a can be in communication (610a) with the external device 630, the second patch 100b can be in communication (610b) with the external device 630, and the third patch 100c can be in communication (610c) with the external device 630. In some embodiments, such an external device can be configured to, for example, coordinate operations of the patches (100a, 100b, 100c), collect data from the patches, etc. In some embodiments, the external device 630 can be configured to communicate with another device at a similar level, with another device at a higher level, or any combination thereof.

Figure 25:
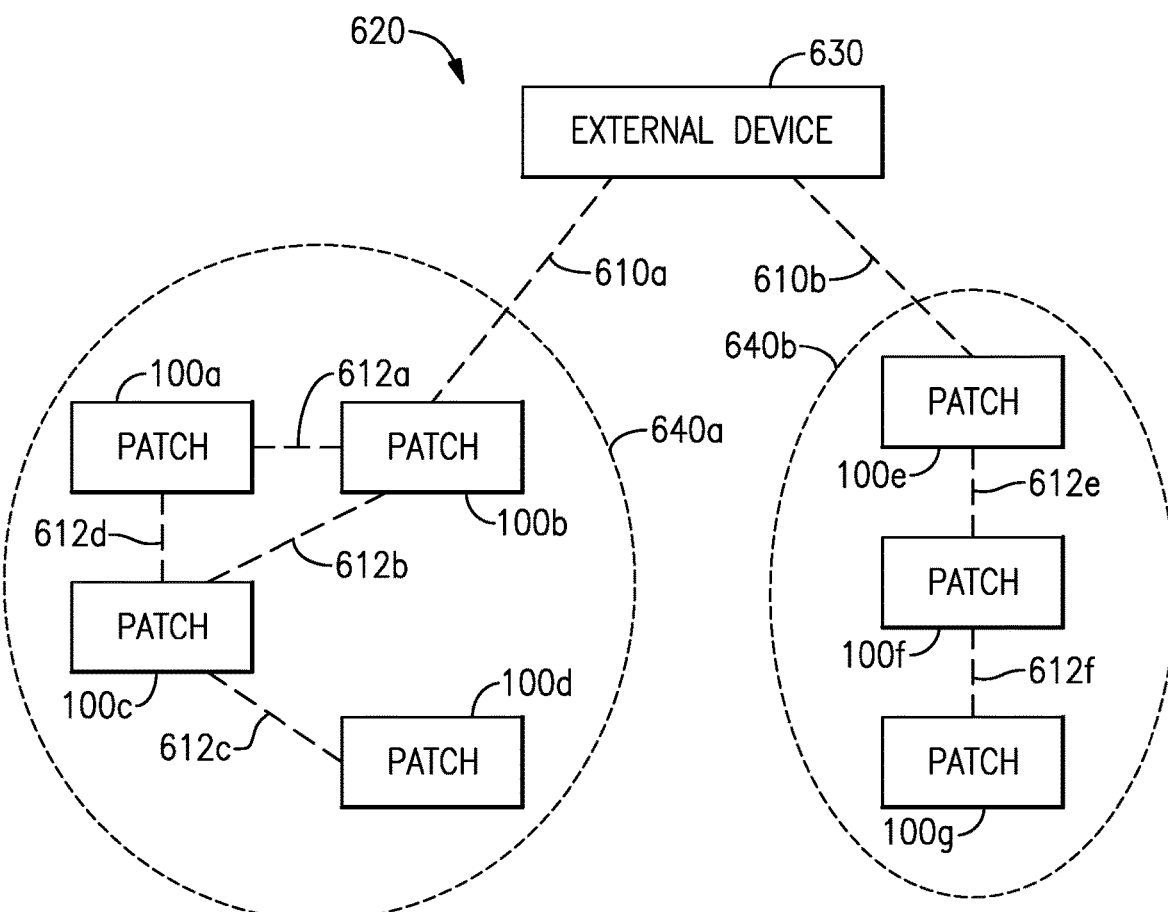
FIG. 25 shows that in some embodiments, the system of FIG. 23 can include a plurality of patches that can communicate with each other, and/or with an external device.

FIG. 25 shows that in some embodiments, the system 620 of FIG. 23 can include a plurality of patches 100 that can communicate with each other, and/or with an external device. For example, a first group (640a) of patches and a second group (640b) are shown to be included in a system 620, and generally in communication with an external device 630. More particularly, the first group 640a is shown to include four example patches 100a, 100b, 100c, 100d, and the second group 640b is shown to include three example patches 100e, 100f, 100g. Such first and second groups 640a, 640b of patches can be grouped based on, for example, physical proximity/separation, different functionalities, etc.

In some embodiments, within a given group, each of the plurality of patches can communicate directly with the external device 630, through a representative patch, or some combination thereon. For example, for the first group 640a, the patches 100a and 100b are shown to have a communication link 612a; the patches 100a and 100c are shown to have a communication link 612d; the patches 100c and 100d are shown to have a communication link 612c; and the patches 100c and 100b are shown to have a communication link 612b. Further, the patch 100b is shown to be a representative communication member and be in communication (610a) with the external device 630.

In another example, for the second group 640b, the patches 100e and 100f are shown to have a communication link 612e; and the patches 100f and 100g are shown to have a communication link 612f. Further, the patch 100e is shown to be a representative communication member and be in communication (610b) with the external device 630.

In some embodiments, the communication links between the patches within a given group can be based on, for example, different patches worn by a given user, relative proximity/distance among the users wearing the respective patches, some hierarchy of the users and/or patches, or some combination thereof. In some embodiments, the communication links between the patches can be configured as a mesh network, or be based on such a network.

In some embodiments, a system of patches as described herein (e.g., in reference to FIGS. 21-25) can provide a system level information that may not be available from an individual patch.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments may be described with reference to equations, algorithms, and/or flowchart illustrations. These methods may be implemented using computer program instructions executable on one or more computers. These methods may also be implemented as computer program products either separately, or as a component of an apparatus or system. In this regard, each equation, algorithm, block, or step of a flowchart, and combinations thereof, may be implemented by hardware, firmware, and/or software including one or more computer program instructions embodied in computer-readable program code logic. As will be appreciated, any such computer program instructions may be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, may be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Some or all of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A system for providing comfort for a person, the system comprising:
a wearable patch configured to be in an inactive state before use, and an active state during use, the wearable patch including a sensor, a support sheet, an activation circuit, and an adhesive layer, the support sheet including a release layer configured to allow the adhesive layer of the wearable patch to be removed from the support sheet, the activation circuit coupled to a pair of surface contacts in the adhesive layer and configured to put the wearable patch in the inactive state conducive to storage based on a first resistance value between the pair of surface contacts having an approximately zero value while the wearable patch is still secured on the release layer including a conductive portion positioned under the pair of surface contacts, the activation circuit further configured to put the wearable patch in the active state based on removal of the release layer in a manner that the pair of surface contacts are no longer in physical contact with the conductive portion in the release layer and a second resistance value approximately infinite or very high compared to the first resistance value exists between the pair of surface contacts, the sensor configured to sense a biological condition of the skin after the wearable patch is attached to the skin of the person based on a measure of a third resistance value at the surface of the skin between the pair of surface contacts, the wearable patch further configured to transmit information representative of the sensed biological condition;
a controller configured to communicate with the wearable patch and perform a pairing process after the sensor transitions from the inactive state to the active state, the controller further configured to receive the information after being paired with the wearable patch and generate a control signal based on the information; and
an adjustment element associated with a furniture item, the adjustment element in communication with the controller and configured to adjust a comfort level of the furniture item for the person in response to the control signal.

2. The system of claim 1, wherein the adjustment element is configured as an accessory to the furniture item.

3. The system of claim 1, wherein the adjustment element is an integral part of the furniture item.

4. The system of claim 1, wherein the furniture item is a bed.

5. The system of claim 4, wherein the adjustment element is configured to provide either or both of cooling and heating for the person based on the sensed biological condition of the skin.

6. The system of claim 1, wherein the controller is implemented as a dedicated device associated with the furniture item.

7. The system of claim 1, wherein the controller is implemented as a dedicated device associated with the adjustment element.

8. The system of claim 1, wherein the controller is implemented as an application software operating in a wireless device.

9. The system of claim 1, wherein the controller is further configured to allow an input from the person to provide feedback for effectiveness of the adjustment of the comfort level to thereby provide a personalized comfort setting for the person.

* * * * *